United States Patent [19]

Stroech et al.

[11] Patent Number: 5,097,047
[45] Date of Patent: Mar. 17, 1992

[54] FUNGICIDAL AND PLANT GROWTH-REGULATING AZOLYLMETHYL-CYCLOPROPYL DERIVATIVES

[75] Inventors: Klaus Stroech, Solingen; Wilhelm Brandes, Leichlingen; Stefan Dutzmann, Duesseldorf, all of Fed. Rep. of Germany

[73] Assignee: Bayer Aktiengesellschaft, Leverkusen, Fed. Rep. of Germany

[21] Appl. No.: 604,559

[22] Filed: Oct. 26, 1990

Related U.S. Application Data

[62] Division of Ser. No. 449,668, Feb. 12, 1989, Pat. No. 4,980,488, which is a division of Ser. No. 206,403, Jun. 14, 1988, Pat. No. 4,913,727.

[30] Foreign Application Priority Data

Jun. 24, 1987 [DE] Fed. Rep. of Germany ....... 3720755
Apr. 19, 1988 [DE] Fed. Rep. of Germany ....... 3812967

[51] Int. Cl.$^5$ ............................................. C07D 303/08
[52] U.S. Cl. ..................................... 549/463; 549/554; 549/559; 549/560; 549/551
[58] Field of Search ............... 549/559, 563, 554, 560, 549/551

[56] References Cited

U.S. PATENT DOCUMENTS 4,548,945 10/1985 Holmwood et al. ................. 549/559
4,551,469 11/1985 Pang et al. ............................. 71/92
4,894,383 1/1990 Holmwood et al. ................. 514/184

*Primary Examiner*—Richard L. Raymond
*Assistant Examiner*—Mark W. Russell
*Attorney, Agent, or Firm*—Sprung Horn Kramer & Woods

[57] ABSTRACT

Fungicidal and plant growth-regulating azolylmethyl-cyclopropyl derivatives of the formula

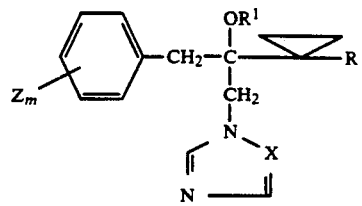

in which
R represents halogen, alkyl or optionally substituted phenyl, or represents the groupings —Y—$R^2$,
wherein
Y represents oxygen, sulphur, SO or $SO_2$ and
$R^2$ represents optionally substituted phenyl,
$R^1$ represents hydrogen, alkyl or acyl,
X represents nitrogen or a CH group,
Z represents halogen, alkyl with 1 to 4 carbon atoms, alkoxy with 1 to 4 carbon atoms, alkylthio with 1 to 4 carbon atoms, halogenoalkyl with 1 or 2 carbon atoms and 1 to 5 halogen atoms, halogenoalkoxy with 1 or 2 carbon atoms and 1 to 5 halogen atoms, halogenoalkylthio with 1 or 2 carbon atoms and 1 to 5 halogen atoms or phenyl which is optionally substituted by alkyl with 1 or 2 carbon atoms and/or halogen, or represents phenoxy which is optionally substituted by alkyl with 1 or 2 carbon atoms and/or halogen and
m represents the number 0, 1, 2 or 3, and addition products thereof with acids and metal salts. Intermediates therefor of the formulas

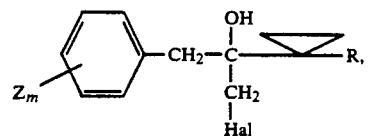

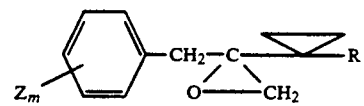

and

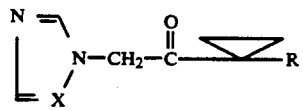

are also new.

4 Claims, No Drawings

FUNGICIDAL AND PLANT GROWTH-REGULATING AZOLYLMETHYL-CYCLOPROPYL DERIVATIVES

This is a division of application Ser. No. 449,668, filed Feb. 12, 1989 now U.S. Pat. No. 4,980,488, which is a division of application Ser. No. 206,403 filed June 12, 1988, now U.S. Pat. No. 4,913,727.

The present invention relates to new azolylmethylcyclopropyl derivatives, several processes for their preparation and their use as fungicides and plant growth regulators.

It is already known that certain azolylmethylcyclopropyl-carbinol derivatives have fungicidal and plant growth-regulating properties (compare EP-OS (European Published Specification) 0,180,136). Thus, for example 1-(4-chlorophenyl)-1-(1-chlorocyclopropyl)-2-(1,2,4-triazol-1-yl)-ethan-1-ol and 1-(4-fluorophenyl)-(1-chloro-cyclopropyl)-2-(1,2,4-triazol-1-yl)-ethan-1-ol can be used for combating fungi and for regulating plant growth. The activity of these substances is good; however, in some cases they leave something to be desired when low amounts are applied.

It is furthermore known that certain hydroxyethyl-azolyl derivatives substituted by cycloalkyl have fungicidal properties (compare EP-OS (European Published Specification) 0,015,756). However, the activity of these substances is also not always completely adequate.

New azolylmethyl-cyclopropyl derivatives of the formula

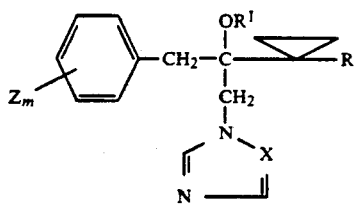

in which
R represents halogen, alkyl or optionally substituted phenyl, or represents the grouping —Y—R², wherein
Y represents oxygen, sulphur, SO or SO₂ and
R² represents optionally substituted phenyl,
R¹ represents hydrogen, alkyl or acyl,
X represents nitrogen or a CH group,
Z represents halogen, alkyl with 1 to 4 carbon atoms, alkoxy with 1 to 4 carbon atoms, alkylthio with 1 to 4 carbon atoms, halogenoalkyl with 1 or 2 carbon atoms and 1 to 5 halogen atoms, halogenoalkoxy with 1 or 2 carbon atoms and 1 to 5 halogen atoms, halogenoalkylthio with 1 or 2 carbon atoms and 1 to 5 halogen atoms or phenyl which is optionally substituted by alkyl with 1 or 2 carbon atoms and/or halogen, or represents phenoxy which is optionally substituted by alkyl with 1 or 2 carbon atoms and/or halogen and
m represents the number 0, 1, 2 or 3, and acid addition salts and metal salt complexes thereof have now been found.

It has furthermore been found that azolylmethylcyclopropyl derivatives of the formula (I) and acid addition salts and metal salt complexes thereof are obtained by a process in which a) propanol derivatives of the formula

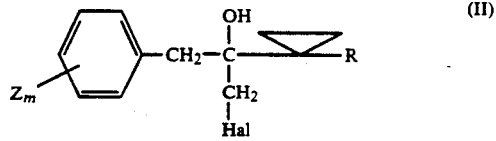

in which
R, Z and m have the abovementioned meaning and
Hal represents chlorine, bromine or iodine, are reacted with azoles of the formula

in which
X has the abovementioned meaning, in the presence of an acid-binding agent and in the presence of a diluent, or b) oxiranes of the formula

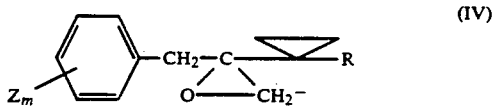

in which
R, Z and m have the abovementioned meaning, are reacted with azoles of the formula

in which
X has the abovementioned meaning, in the presence of an acid-binding agent and in the presence of a diluent, or c) azolylmethyl-ketones of the formula

in which
R and X have the above-mentioned meaning, are reacted with organometallic compounds of the formula

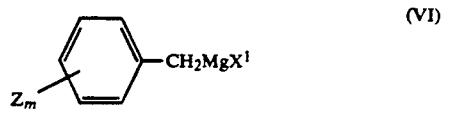

in which
Z and m have the above-mentioned meaning and $X^1$ represents chlorine, bromine or iodine, in the presence of a diluent, or d) azolylmethyl-cyclopropyl-carbinol derivatives of the formula

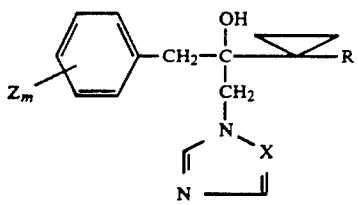

(Ia)

in which

R, X, Z and m have the abovementioned meaning, are reacted with strong bases in the presence of a diluent, and the alcoholates thereby formed, of the formula

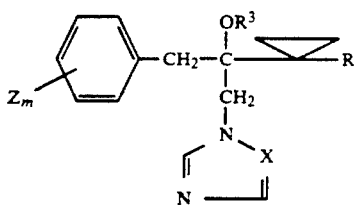

(Ib)

in which

R, X, Z and m have the abovementioned meaning and
$R^3$ represents a cationic radical of a base, are reacted with halogen compounds of the formula $$R^4-Hal'$$ (VII)

in which $R^4$ represents alkyl or acyl and

Hal' represents halogen, in the presence of a diluent, and, if appropriate, an acid or a metal salt is then added onto the compounds of the formula (I) thus obtained.

Finally, it has been found that the new azolylmethyl-cyclopropyl derivatives of the formula (I) and acid addition salts and metal salt complexes thereof have powerful fungicidal and plant growth-regulating properties.

The substances according to the invention contain an asymmetrically substituted carbon atom. They can therefore be obtained in optical isomer forms. The present invention relates both to the individual isomers and to mixtures thereof.

Surprisingly, the substances according to the invention have a better fungicidal and plant growth-regulating activity than the already known compounds which are structurally the most similar and have the same type of action.

Formula (I) provides a general definition of the azolylmethyl-cyclopropyl derivatives according to the invention. Preferably, in this formula, R represents fluorine, chlorine, bromine or alkyl with 1 to 6 carbon atoms, or represents phenyl which is optionally substituted by halogen, halogenoalkyl with 1 or 2 carbon atoms and 1 to 5 halogen atoms, alkyl with 1 to 4 carbon atoms and/or alkoxy with 1 to 4 carbon atoms, or represents the grouping —Y—$R^2$, wherein Y represents oxygen, sulphur, SO or $SO_2$ and $R^2$ represents phenyl which is optionally substituted by halogen, halogenoalkyl with 1 or 2 carbon atoms and 1 to 5 halogen atoms, alkyl with 1 to 4 carbon atoms and/or alkoxy with 1 to 4 carbon atoms, $R^1$ represents hydrogen, alkyl with 1 to 6 carbon atoms or alkylcarbonyl with 1 to 6 carbon atoms in the alkyl group, X represents nitrogen or a CH group, Z represents fluorine, chlorine, bromine, methyl, ethyl, isopropyl, tert.-butyl, methoxy, methylthio, trifluoromethyl, trifluoromethoxy, trifluoromethylthio or phenyl which is optionally substituted by fluorine, chlorine and/or methyl, or represents phenoxy which is optionally substituted by fluorine, chlorine and/or methyl and m represents the number 0, 1, 2 or 3.

If m represents the number 2 or 3, the radicals represented by Z can be identical or different.

Particularly preferred compounds of the formula (I) are those in which

R represents fluorine, chlorine, bromine, methyl, ethyl or phenyl which is optionally substituted by one to three identical or different substituents from the group comprising fluorine, chlorine, bromine, trifluoromethyl, methyl, ethyl, methoxy and/or ethoxy, or represents the grouping —Y—$R^2$, wherein Y represents oxygen, sulphur, SO or $SO_2$ and $R^2$ represents phenyl which is optionally substituted by one to three identical or different substituents from the group comprising fluorine, chlorine, bromine, trifluoromethyl, methyl, ethyl, methoxy and/or ethoxy, $R^1$ represents hydrogen, methyl, ethyl, n-propyl, isopropyl, n-butyl, isobutyl, methylcarbonyl, ethylcarbonyl, n-propylcarbonyl, isopropyl-carbonyl, n-butyl-carbonyl or isobutyl-carbonyl, X represents nitrogen or a CH group, Z represents fluorine, chlorine, bromine, methyl, ethyl, isopropyl, tert.-butyl, methoxy, methylthio, trifluoromethyl, trifluoromethoxy, trifluoromethylthio or phenyl which is optionally substituted by fluorine, chlorine and/or methyl, or represents phenoxy which is optionally substituted by fluorine, chlorine and/or methyl and m represents the number 0, 1, 2 or 3.

Addition products of acids and those azolyl-methyl-cyclopropyl derivatives of the formula (I) in which R, $R^1$, X, Z and m have the meanings which have already been mentioned as preferred for these radicals and this index are also preferred compounds according to the invention.

The acids which can be added on include, preferably, hydrogen halide acids, such as, for example, hydrochloric acid and hydrobromic acid, in particular hydrochloric acid, and furthermore phosphoric acid, nitric acid, sulphuric acid, mono- and bifunctional carboxylic acids and hydroxycarboxylic acids, such as, for example, acetic acid, maleic acid, succinic acid, fumaric acid, tartaric acid, citric acid, salicylic acid, sorbic acid and lactic acid, and sulphonic acids, such as, for example, p-toluenesulphonic acid, 1,5-naphthalenedisulphonic acid or camphorsulphonic acid.

Addition products of salts of metals of main groups II to IV and of sub-groups I and II and IV to VIII of the periodic table of the elements and those azolyl-methyl-cyclopropyl derivatives of the formula (I) in which R, $R^1$, X, Z and m have the meanings which have already been mentioned as preferred for these radicals and this index are also preferred compounds according to the invention.

Salts of copper, zinc, manganese, magnesium, tin, iron and nickel are particularly preferred here. Possible anions of these salts are those which are derived from those acids which lead to physiologically acceptable addition products. Particularly preferred acids of this type are, in this connection, the hydrogen halide acids, such as, for example, hydrochloric acid and hydrobromic acid, and furthermore phosphoric acid, nitric acid and sulphuric acid.

The substances listed in the following table may be mentioned as examples of azolylmethyl-cyclopropyl derivatives of the formula (I).

TABLE

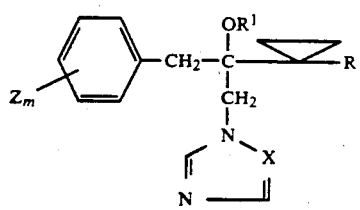
(I)

| $Z_m$ | $R^1$ | X | R |
|---|---|---|---|
| 4-Cl | H | N | Cl |
| 2,4-Cl$_2$ | " | " | Cl |
| 2,4-F$_2$ | " | " | Cl |
| 4-CH$_3$ | " | " | Cl |
| 4-CF$_3$ | " | " | Cl |
| 4-OCF$_3$ | " | " | Cl |
| 4-OCH$_3$ | " | " | Cl |
| 4-SCH$_3$ | " | " | Cl |
| 2,4,6-Cl$_3$ | " | " | Cl |
| 4-Cl | " | " | F |
| 4-Cl | " | CH | Cl |
| 4-Cl | CH$_3$ | N | Cl |
| 4-Cl | H | " | ⌬ |
| 4-Cl | " | " | —O—⌬ |
| 4-Cl | " | " | —S—⌬ |
| 4-Cl | " | " | —SO—⌬ |
| 4-Cl | " | " | —SO$_2$—⌬ |

TABLE-continued

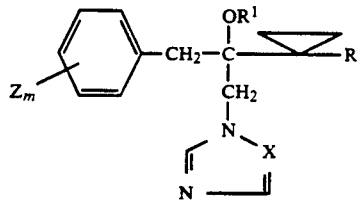
(I)

| $Z_m$ | $R^1$ | X | R |
|---|---|---|---|
| 4-⌬ | " | " | Cl |
| 4-O-⌬ | " | " | Cl |
| 4-C$_4$H$_9$-t. | " | " | Cl |
| 2-Cl, 4-CH$_3$ | " | " | Cl |
| — | " | " | Cl |
| 4-Cl | —CO—CH$_3$ | " | Cl |
| 4-Cl | —C$_2$H$_5$ | " | Cl |
| 4-F | CH$_3$ | " | F |
| 4-Cl | H | " | CH$_3$ |

If 1-chloro-2-(1-chlorocyclopropyl)-3-(4-fluorophenyl)-propan-2-ol and 1,2,4-triazole are used as starting substances, the course of process (a) according to the invention can be illustrated by the following equation:

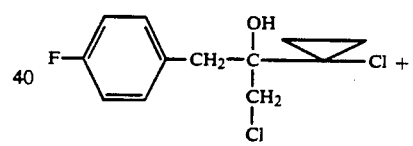

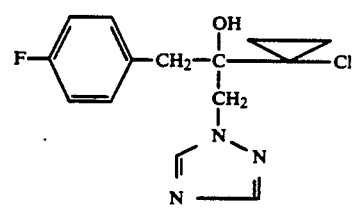

If 2-[(4-fluorophenyl)-methyl]-2-(1-chloro-cyclopropyl)-oxirane and 1,2,4-triazole are used as starting substances, the course of process (b) according to the invention can be illustrated by the following equation:

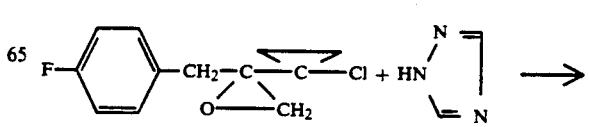

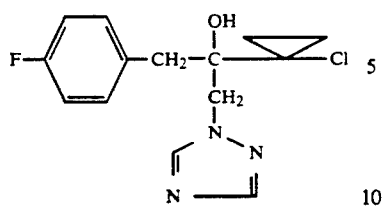

If (1,2,4-triazol-1-yl-methyl)-(1-chloro-cycloprop-1-yl)-ketone and 4-fluorobenzyl-magnesium bromide are used as starting substances, the course of the process (c) according to the invention can be illustrated by the following equation:

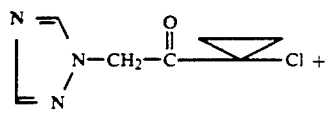

If 1-(4-fluorophenyl)-2-(1-chlorocyclopropyl)-3-(1,2,4-triazol-1-yl)-propan-2-ol and sodium hydride are used as starting substances and iodomethane is used as the reaction component, the course of process (d) according to the invention can be illustrated by the following equation:

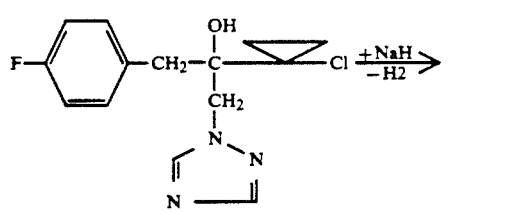

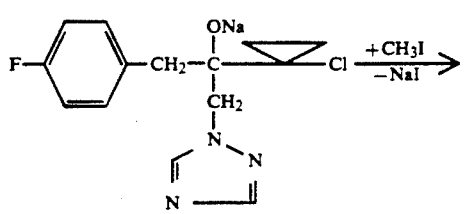

Formula (II) provides a general definition of the propanol derivatives required as starting substances in process (a) according to the invention. In this formula, R, Z and m preferably have those meanings which have already been mentioned as preferred for these radicals and this index in connection with the description of the substances of the formula (I) according to the invention. Hal preferably represents chlorine or bromine.

The propanol derivatives of the formula (II) are as yet still unknown. They can be prepared by a process in which cyclopropyl ketones of the formula

 (VIII)

in which
R has the abovementioned meaning and
Hal" represents chlorine or bromine, are reacted with organometallic compounds of the formula

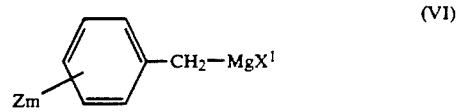 (VI)

in which
$X^1$, Z and m have the abovementioned meaning, in the presence of a diluent.

The cyclopropyl ketones of the formula (VIII) required as starting substances in the preparation of the propanol derivatives by the above process are known in some cases. They can be prepared by a process in which ketones of the formula

 (IX)

in which
R has the abovementioned meaning, are reacted with chlorinating agents or brominating agents in the presence of a diluent.

The ketones of the formula (IX) required as starting substances in the preparation of cyclopropyl ketones of the formula (VIII) are known or can be synthesized by processes which are known in principle (compare Synthesis 1977, 189).

Possible chlorinating agents and brominating agents in the above process for the preparation of cyclopropyl ketones of the formula (VIII) are all the chlorinating and brominating reagents which are customary for such reactions. Sulphuryl chloride, sulphuryl bromide and bromine can preferably be used.

Possible diluents in the preparation of cyclopropyl ketones of the formula (VIII) by the above process are all the inert organic solvents which are customary for such reactions. Solvents which can preferably be used are halogenated aliphatic hydrocarbons, such as methylene chloride, chloroform and carbon tetrachloride.

The temperatures can be varied within a certain range in the above process for the preparation of cyclopropyl ketones of the formula (VIII). The process is in general carried out at temperatures between −10° C. and +60° C., preferably between 0° C. and +40° C.

The above process for the preparation of cyclopropyl ketones of the formula (VIII) is in general carried out under normal pressure. However, it is also possible for the process to be carried out under increased or reduced pressure.

In carrying out the above process for the preparation of cyclopropyl ketones of the formula (VIII), in general a stoichiometric amount or a slight excess of chlorinating or brominating agent is employed per mol of ketone of the formula (IX). Working up is by customary methods. A procedure is in general followed in which the reaction mixture is washed with dilute aqueous sodium bicarbonate solution and with water in succession and is then dried and concentrated.

The organometallic compounds of the formula (VI) required as reaction components in the above process for the preparation of propanol derivatives of the formula (II) are known or can be synthesized by methods which are known in principle. Thus, compounds of the formula (VII) are obtained by a process in which benzyl halides of the formula

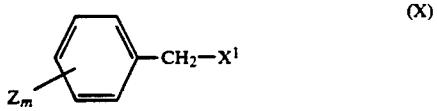

in which

X$^1$, Z and m have the abovementioned meaning, are reacted with magnesium in the presence of an inert diluent, such as, for example, diethyl ether, at temperatures between 0° C. and 50° C.

The benzyl halides of the formula (X) are generally known compounds of organic chemistry.

Possible diluents in the above process for the preparation of propanol derivatives of the formula (II) are all the inert organic solvents which are customary for such reactions. Solvents which can preferably be used are ethers, such as diethyl ether, tetrahydrofuran and dioxane.

The reaction temperatures can be varied within a certain range in carrying out the above process for the preparation of propanol derivatives of the formula (II). The reaction is in general carried out at temperatures between −80° C. and +50° C., preferably between −80° C. and 40° C.

The above process for the preparation of propanol derivatives of the formula (II) is in general carried out under normal pressure. However, it is also possible for the process to be carried out under increased or reduced pressure.

In carrying out the above process for the preparation of propanol derivatives of the formula (II), in general 1 to 1.2 mols of organometallic compound of the formula (VI) are employed per mol of cyclopropyl ketone of the formula (VIII) and are advantageously prepared immediately beforehand and further processed in situ. Working up is by customary methods. A procedure is in general followed in which the reaction mixture is first acidified, water is added and the organic phase is then separated off, washed and, after drying, concentrated.

The azoles of the formula (III) required as reaction components for carrying out process (a) according to the invention are generally known compounds of organic chemistry.

Possible acid-binding agents in carrying out process (a) according to the invention are all the customary inorganic and organic bases. Bases which can preferably be used are alkali metal carbonates, such as sodium carbonate and potassium carbonate, and furthermore alkali metal hydroxides, such as sodium hydroxide and potassium hydroxide, and in addition alkali metal alcoholates, such as sodium methylate and ethylate and potassium methylate and ethylate and potassium tert.-butylate, and moreover lower tertiary alkylamines, cycloalkylamines and aralkylamines, such as, in particular, triethylamine.

Possible diluents in carrying out process (a) according to the invention are all the customary inert organic solvents. Solvents which can preferably be used are nitriles, such as acetonitrile, and furthermore aromatic hydrocarbons, such as benzene, toluene and dichlorobenzene, and also formamides, such as dimethylformamide, as well as strongly polar solvents, such as dimethyl sulphoxide and hexamethylphosphoric acid triamide.

The reaction temperatures can be varied within a substantial range in carrying out process (a) according to the invention. The reaction is in general carried out at temperatures between 0° C. and 200° C., preferably between 60° C. and 150° C.

Process (a) according to the invention, like processes (b), (c) and (d) according to the invention, is in general carried out under normal pressure. However, it is in each case also possible to carry out the process under increased or reduced pressure.

In carrying out process (a) according to the invention, in general 1 to 4 mols of azole of the formula (III) and 1 to 3 mols of acid-binding agent are employed per mol of propanol derivative of the formula (II). In some cases, it is advantageous to work under an inert gas atmosphere. Working up is by customary methods. A procedure is in general followed in which the reaction mixture is concentrated by stripping off the diluent, the residue which remains is taken up in an organic solvent of low water-miscibility and the organic phase is washed and, after drying, concentrated. If appropriate, the product which remains can be subjected to further purification processes.

Formula (IV) provides a general definition of the oxiranes required as starting substances in process (b) according to the invention. In this formula, R, Z and m preferably have those meanings which have already been mentioned as preferred for these radicals and this index in connection with the description of the substances of the formula (I) according to the invention.

The oxiranes of the formula (IV) are as yet still unknown. They can be prepared by a process in which propanol derivatives of the formula

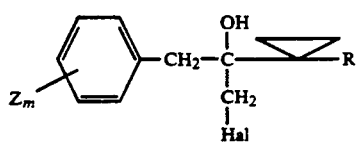

in which

R, Z, Hal and m have the abovementioned meaning, are reacted with bases in the presence of a diluent.

Possible bases in the preparation of oxiranes of the formula (IV) by the above process are all the inorganic and organic bases which are usually suitable for such reactions. All those bases which have already been mentioned as preferred acid-binding agents in connection with the description of process (a) according to the invention can preferably be used.

The reaction temperatures can be varied within a certain range in the preparation of oxiranes by the above process. The reaction is in general carried out at temperatures between 0° C. and 100° C., preferably between 20° C. and 60° C.

The above process for the preparation of oxiranes of the formula (IV) is in general carried out under normal pressure. However, it is also possible for the process to be carried out under increased or reduced pressure.

In carrying out the above process for the preparation of oxiranes of the formula (IV), in general 1 to 3 mols of base are employed per mol of propanol derivative of the formula (II). Working up is by customary methods.

Possible acid-binding agents and diluents in carrying out process (b) according to the invention are all the acid-binding agents and diluents which can usually be employed for such reactions. All those acid-binding agents and diluents which have already been mentioned as preferred acid-binding agents and diluents in connection with the description of process (a) according to the invention can preferably be used.

The reaction temperatures can be varied within a substantial range in carrying out process (b) according to the invention. The reaction is in general carried out at temperatures between 0° C. and 200° C., preferably between 60° C. and 150° C.

In carrying out process (b) according to the invention, in general 1 to 2 mols of azole of the formula (III) and 1 to 2 mols of acid-binding agent are employed per mol of oxirane of the formula (IV). Working up is by customary methods.

Formula (V) provides a general definition of the azolylmethyl ketones required as starting substances in process(c) according to the invention. In this formula, R and X preferably have those meanings which have already been mentioned as preferred for these radicals in connection with the description of the substances of the formula (I) according to the invention. The azolylmethyl ketones of the formula (V) are as yet still unknown. They can be prepared by a process in which cyclopropyl ketones of the formula

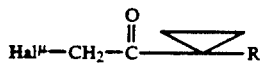 (VIII)

in which

R and Hal" have the above-mentioned meaning, are reacted with azoles of the formula

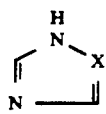 (III)

in which

X has the above-mentioned meaning, in the presence of an acid-binding agent and, if appropriate, in the presence of a diluent.

Possible acid-binding agents and diluents in the preparation of azolylmethyl ketones of the formula (V) by the above process are all acid-binding agents and diluents which are customary for such reactions. All those acid-binding agents which have already been mentioned as preferred acid-binding agents in connection with the description of process (a) according to the invention can preferably be used. Ketones, such as acetone, and nitriles such as acetonitrile, can preferably be used as diluents.

The reaction temperatures can be varied within a substancial range in the preparation of azolylmethyl ketones of the formula (V) by the above process. The reaction is in general carried out at temperatures between 0° C. and 120° C., preferably between 20° C. and 100° C.

The above process for the preparation of azolylmethyl ketones of the formula (V) is in general carried out under normal pressure, In carrying out the above process for the preparation of azolylmethyl ketones of the formula (V), in general 1 to 4 mols of azole of the formula (III) as well as 1 to 3 mols of acid-binding agent are employed per mol of cyclopropyl ketone of the formula (VIII).

The organometallic compounds of the formula (VI) required as reaction components in process (c) according to the invention have already been mentioned in connection with the description of the process for the preparation of the propanol derivatives of the formula (II).

Possible diluents in carrying out process (c) according to the invention are all customary inert organic solvents. Ethers, such as diethylether, tetrahydrofurane and dioxane, can preferably be used.

The reaction temperatures can be varied within a substancial range in carrying out process (c) according to the invention. The reaction is in general carried out at temperatures between −80° C. and +60° C., preferably between −70° C. and +50° C.

In carrying out process (c) according to the invention, in general 0.8 to 1 mol of an organometallic compound of the formula (VI), which advantageously is prepared immediately before and is further reacted in situ, are employed per mol of azolylmethyl ketone of the formula (V). Working up is by customary methods.

The azolylmethylcyclopropyl derivatives of the formula (Ia) required as starting substances in process (d) according to the invention are compounds according to the invention. They are converted into the corresponding alcoholates in a generally known manner by reaction with suitable strong bases, such as alkali metal amides or hydrides, quaternary ammonium hydroxides or phosphonium hydroxides, in an inert diluent, such as, for example, dioxane, at room temperature. $R^3$ in the compounds of the formula (Ib) accordingly preferably represents an alkali metal cation, such as a sodium or potassium cation, or represents a quaternary ammonium or phosphonium cation.

Formula (VII) provides a general definition of the halogen compounds also required as starting substances in process (d) according to the invention. In this formula, $R^4$ preferably has those meanings which have already been mentioned as preferred for the substituent $R^1$ in connection with the description of the substances of the formula (I) according to the invention, with the exception of the meaning of hydrogen. Hal' preferably represents chlorine, bromine or iodine.

The halogen compounds of the formula(VII) are known or can be prepared by methods which are known in principle.

Possible diluents in carrying out process (d) according to the invention are inert organic solvents. These include, preferably, ethers, such as diethyl ether or dioxane; aromatic hydrocarbons, such as benzene; in individual cases also chlorinated hydrocarbons, such as chloroform, methylene chloride or carbon tetrachloride; and hexamethylphosphoric acid triamide.

The reaction temperatures can be varied within a substantial range in carrying out process (d) according to the invention. The reaction is in general carried out between 0° C. and 120° C., preferably between 20° C. and 100° C.

In carrying out process (d) according to the invention, hydroxy compounds of the formula (Ia) are first reacted with strong bases to give the corresponding alcoholates of the formula (Ib). In the subsequent stage, 1 to 2 mols of halogen compound of the formula (VII) are preferably employed per mol of an alcoholate of the formula (Ib). To isolate the end products, the reaction mixture is freed from the solvent, and water and an organic solvent are added to the residue. The organic phase is separated off, worked up in the customary manner and purified.

In a preferred embodiment, a procedure is advantageously followed in which a hydroxy compound of the formula (Ia) is used as the starting substance, this is converted into the alkali metal alcoholate by means of an alkali metal hydride or alkali metal amide in a suitable organic solvent, and the alcoholate is reacted immediately, without being isolated, with a halogen compound of the formula(VII), the compounds of the formula (I) according to the invention being obtained in one operation, an alkali metal halide being eliminated.

According to another preferred embodiment, the preparation of the alcoholates and the reaction with a halogen compound of the formula(VII) are advantageously carried out in a two-phase system, such as, for example, aqueous sodium hydroxide solution or potassium hydroxide solution/toluene or methylene chloride, with the addition of 0.01–1 mol of a phase transfer catalyst, such as, for example, ammonium or phosphonium compounds, the reaction between the alcoholates and the halides in the organic phase taking place in the organic phase or at the phase boundary.

The azolylmethyl-cyclopropyl derivatives of the formula (I) obtainable by the processes according to the invention can be converted into acid addition salts or metal salt complexes.

Those acids which have already been mentioned as preferred acids in connection with the description of the acid addition salts according to the invention can preferably be used to prepare acid addition salts of the compounds of the formula (I).

The acid addition salts of the compounds of the formula (I) can be obtained in a simple manner by customary salt formation methods, for example by dissolving a compound of the formula (I) in a suitable inert solvent and adding the acid, for example hydrochloric acid, and can be isolated in a known manner, for example by filtration, and if appropriate purified by washing with an inert organic solvent.

Those salts of metals which have already been mentioned as preferred metal salts in connection with the description of the metal salt complexes according to the invention can preferably be used to prepare metal salt complexes of the compounds of the formula (I).

The metal salt complexes of the compounds of the formula (I) can be obtained in a simple manner by customary processes, thus, for example, by dissolving the metal salt in alcohol, for example ethanol, and adding the solution to compounds of the formula (I). The metal salt complexes can be isolated in a known manner, for example by filtration, and if appropriate purified by recrystallization.

The active compounds according to the invention have a powerful microbicidal action and can be used as fungicides.

Fungicidal agents in plant protection are employed for combating Plasmodiophoromycetes, Oomycetes, Chytridiomycetes, Zygomycetes, Ascomycetes, Basidiomycetes and Deuteromycetes.

Some causative organisms of fungal and bacterial diseases which come under the generic names listed above may be mentioned as examples, but not by way of limitation: Xanthomonas species, such as *Xanthomonas oryzae*; Pseudomonas species, such as *Pseudomonas lachrymans*; Erwinia species, such as *Erwinia amylovora*; Pythium species, such as *Pythium ultimum*; Phytophthora species, such as *Phytophthora infestans*; Pseudoperonospora species, such as *Pseudoperonospora humuli* or *Pseudoperonospora cubense*; Plasmopara species, such as *Plasmopara viticola*; Peronospora species, such as *Peronospora pisi* or *P. brassicae*; Erysiphe species, such as *Erysiphe graminis*; Sphaerotheca species, such as *Sphaerotheca fuliginea*; Podosphaera species, such as *Podosphaera leucotricha*; Venturia species, such as *Venturia inaequalis*; Pyrenophora species, such as *Pyrenophora teres* or *P. graminea* (conidia form: Drechslera, syn: Helminthosporium); Cochliobolus species, such as *Cochliobolus sativus* (conidia form: Drechslera, syn: Helminthosporium); Uromyces species, such as *Uromyces appendiculatus*; Puccinia species, such as *Puccinia recondita*; Tilletia species, such as *Tilletia caries*; Ustilago species, such as *Ustilago nuda* or *Ustilago avenae*; Pellicularia species, such as *Pellicularia sasakii*; Pyricularia species, such as *Pyricularia oryzae*; Fusarium species, such as *Fusarium culmorum*; Botrytis species, such as *Botrytis cinerea*; Septoria species, such as *Septoria nodorum*; Leptosphaeria species, such as *Leptosphaeria nodorum*; Cercospora species, such as *Cercospora canescens*; Alternaria species, such as *Alternaria brassicae*, Pseudocercosporella species, such as *Pseudocercosporella herpotrichoides*.

The good toleration, by plants, of the active compounds, at the concentrations required for combating plant diseases, permits treatment of above-ground parts of plants, of vegetative propagation stock and seeds, and of the soil.

The active compounds according to the invention are particularly suitable for combating cereal diseases and rice diseases, such as Pseudocercosporella, and for combating Uromyces and Botrytis in pomiculture, viticulture and vegetable growing.

They can be used with particularly good success against Pyricularia on rice and against *Leptosphaeria nodorum*, *Pyrenophora teres* and rust and mildew in cereal crops. The substances according to the invention also exhibit a good in vitro action.

The active compounds according to the invention furthermore also have plant growth-regulating properties.

The active compounds according to the invention engage in the metabolism of the plants and can therefore be employed as growth regulators.

Experience to date of the mode of action of plant growth regulators has shown that an active compound can also exert several different actions on plants. The actions of the compounds depend essentially on the point in time at which they are used, relative to the stage of development of the plant, and on the amounts of active compound applied to the plants or their environment and the way in which the compounds are applied. In every case, growth regulators are intended to influence the crop plants in the particular manner desired.

Plant growth-regulating compounds can be employed, for example, to inhibit vegetative growth of the plants. Such inhibition of growth is, inter alia, of economic interest in the case of grasses, since it is thereby possible to reduce the frequency of cutting the grass in ornamental gardens, parks and sportsgrounds, on verges, at airports or in fruit orchards. The inhibition of growth of herbaceous and woody plants on verges and in the vicinity of pipelines or overland lines or, quite generally, in areas in which heavy additional growth of plants is undesired, is also of importance.

The use of growth regulators to inhibit the growth in length of cereals is also important. The danger of bending ("lodging") of the plants before harvesting is thereby reduced or completely eliminated. Furthermore, growth regulators can strengthen the stem of cereals, which again counteracts lodging. The use of growth regulators for shortening and strengthening the stem enables higher amounts of fertilizer to be applied to increase the yield, without danger of the cereal lodging.

In the case of many crop plants, inhibition of the vegetative growth makes denser planting possible, so that greater yields per area of ground can be achieved. An advantage of the smaller plants thus produced is also that the crop can be worked and harvested more easily.

Inhibition of the vegetative growth of plants can also lead to increases in yield, since the nutrients and assimilates benefit blossoming and fruit formation to a greater extent than they benefit the vegetative parts of plants.

Promotion of vegetative growth can also frequently be achieved with growth regulators. This is of great utility if it is the vegetative parts of the plants which are harvested. Promoting the vegetative growth can, however, also simultaneously lead to a promotion of generative growth, since more assimilates are formed, so that more fruit, or larger fruit, is obtained.

Increases in yield can in some cases be achieved by affecting the plant metabolism, without noticeable changes in vegetative growth. A change in the composition of plants, which in turn can lead to a better quality of the harvested products, can furthermore be achieved with growth regulators. Thus it is possible, for example, to increase the content of sugar in sugar beets, sugar cane, pineapples and citrus fruit or to increase the protein content in soy beans or cereals. Using growth regulators it is also possible, for example, to inhibit the degradation of desired constituents, such as, for example, sugar in sugar beets or sugar cane, before or after harvesting. It is also possible favorably to influence the production or the efflux of secondary plant constituents. The stimulation of latex flux in rubber trees may be mentioned as an example.

Parthenocarpous fruit can be formed under the influence of growth regulators. Furthermore, the gender of the flowers can be influenced. Sterility of the pollen can also be produced, which is of great importance in the breeding and preparation of hybrid seed.

Branching of plants can be controlled by using growth regulators. On the one hand, by breaking the apical dominance the development of side shoots can be promoted, which can be very desirable, especially in the cultivation of ornamental plants, also in connection with growth inhibition. On the other hand, however, it is also possible to inhibit the growth of side shoots. There is great interest in this action, for example, in the cultivation of tobacco or in the planting of tomatoes.

The amount of leaf on plants can be controlled, under the influence of growth regulators, so that defoliation of the plants at a desired point in time is achieved. Such defoliation is of great importance in the mechanical harvesting of cotton, but is also of interest for facilitating harvesting in other crops, such as, for example, in viticulture. Defoliation of the plants can also be carried out to lower the transpiration of the plants before they are transplanted.

The shedding of fruit can also be controlled with growth regulators. On the one hand, it is possible to prevent premature shedding of fruit. However, on the other hand, sheeding of fruit, or even the fall of blossom, can also be promoted up to a certain degree ("thinning out") in order to interrupt the alternance. By alternance there is understood the peculiarity of some species of fruit to produce very different yields from year to year, for endogenic reasons. Finally, using growth regulators it is possible to reduce the force required to detach the fruit at harvest time so as to permit mechanical harvesting or facilitate manual harvesting.

Using growth regulators, it is furthermore possible to achieve an acceleration or retardation of ripening of the harvest product, before or after harvesting. This is of particular advantage, since it is thereby possible to achieve optimum adaptation to market requirements. Furthermore, growth regulators can in some cases improve the coloration of fruit. In addition, concentrating the ripening within a certain period of time is also achievable with the aid of growth regulators. This provides the preconditions for being able to carry out complete mechanical or manual harvesting in only a single pass, for example in the case of tobacco, tomatoes or coffee.

Using growth regulators, it is furthermore possible to influence the latent period of seeds or buds of plants, so that the plants, such as, for example, pineapple or ornamental plants in nurseries, germinate, shoot or blossom at a time at which they normally show no readiness to do so. Retarding the shooting of buds or the germination of seeds with the aid of growth regulators can be desirable in regions where frost is a hazard, in order to avoid damage by late frosts.

Finally, the resistance of plants to frost, drought or a high salt content in the soil can be induced with growth regulators. Cultivation of plants in regions which are usually unsuitable for this purpose thereby becomes possible.

The active compounds can be converted to the customary formulations, such as solutions, emulsions, suspensions, powders, foams, pastes, granules, aerosols, very fine capsules in polymeric substances and in coating compositions for seed, and ULV formulations.

These formulations are produced in known manner, for example by mixing the active compounds with extenders, that is, liquid solvents, liquefied gases under pressure, and/or solid carriers, optionally with the use of surface-active agents, that is, emulsifying agents and/or dispersing agents and/or foam-forming agents. In the case of the use of water as an extender, organic solvents can, for example, also be used as auxiliary solvents. As liquid solvents, there are suitable in the main: aromatics, such as xylene, toluene or alkyl naphthalenes, chlorinated aromatics or chlorinated aliphatic hydrocarbons, such as chlorobenzenes, chloroethylenes or methylene chloride, aliphatic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, strongly polar solvents, such as dimethylformamide and dimethylsulphoxide, as well as water; by liquefied gaseous extenders or carriers are meant liquids which are gaseous at normal temperature and under normal pressure, for example aerosol propellants, such as halogenated hydrocarbons as well as butane, propane, nitrogen and carbon dioxide; as solid carriers there are suitable: for example ground natural minerals, such as kaolins, clays, talc, chalk, quartz, attapulgite, montmorillonite or diatomaceous earth, and ground synthetic minerals, such as highly dispersed silicic acid, alumina and silicates; as solid carriers for granules there are suitable: for example crushed and fractionated natural rocks such as calcite, marble, pumice, sepiolite and dolomite, as well as synthetic granules of inorganic and organic meals, and granules of organic material such as sawdust, coconut shells, corn cobs and tobacco stalks; as emulsifying and/or foam-forming agents there are suitable: for example non-ionic and anionic emulsifiers, such as polyoxyethylene-fatty acid esters, polyoxyethylene-fatty alcohol ethers, for example alkylaryl polyglycol ethers, alkyl sulphonates, alkyl sulphates, aryl sulphonates as well as albumin hydrolysis products; as dispersing agents there are suitable: for example ligninsulphite waste liquors and methylcellulose.

Adhesives such as carboxymethylcellulose and natural and synthetic polymers in the form of powders, granules or latices, such as gum arabic, polyvinyl alcohol and polyvinyl acetate, as well as natural phospholipids, such as cephalins and lecithins, and synthetic phospholipids, can be used in the formulations. Other additives can be mineral and vegetable oils.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations in general contain between 0.1 and 95 percent by weight of active compound, preferably between 0.5 and 90%.

The active compounds according to the invention can be present in the formulations as a mixture with other known active compounds, such as fungicides, insecticides, acaricides and herbicides, and in mixtures with fertilizers and other growth regulators.

The active compounds can be used as such or in the form of their formulations or the use forms prepared therefrom, such as ready-to-use solutions, emulsifiable concentrates, emulstions, foams, suspensions, wettable powders, pastes, soluble powders, dusts and granules.

They are used in the customary manner, for example by watering, spraying, atomizing, scattering, dusting, foaming, brushing on and the like. It is furthermore possible to apply the active compounds by the ultra-low volume method or to inject the active compound formulation or the active compound itself into the soil. The seed of the plants can also be treated.

When the substances according to the invention are used as fungicides, the amount applied can be varied within a substantial range, depending on the type of application. In the treatment of parts of plants, the active compound concentrations in the use forms are thus in general between 1 and 0.0001% by weight, preferably between 0.5 and 0.001%. In the treatment of seed, amounts of active compound of 0.001 to 50 g per kilogram of seed, preferably 0.01 to 10 g, are generally required. For the treatment of soil, active compound concentrations of 0.00001 to 0.1% by weight, preferably 0.0001 to 0.02%, are required at the place of action.

When the compounds according to the invention are used as plant growth-regulators, the amounts applied can be varied within a substantial range. In general, 0.01 to 50 kg, preferably 0.05 to 10 kg of active compound are used per hectare of soil surface.

When the substances according to the invention are used as plant growth regulators, the rule is that the application is carried out in a preferred period of time, the exact definition of which depends on the climatic and vegetative circumstances.

The preparation and the use of the active compounds according to the invention can be seen from the following examples.

PREPARATION EXAMPLES

EXAMPLE 1

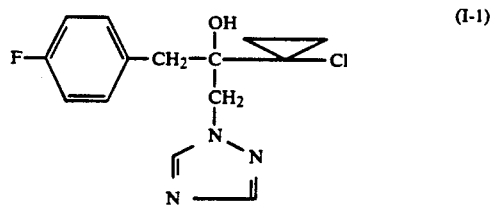

(I-1)

Process a:

65 g (0.94 mol) of 1,2,4-triazole and 71 g (0.63 mol) of potassium tert.-butylate are taken in 160 ml of absolute dimethylformamide under a nitrogen atmosphere and are heated to 80° C. A solution of 70.6 g (0.26 mol) of 1-chloro-2-(1-chlorocyclopropyl)-3-(4-fluorophenyl)-propan-2-ol in 90 ml of absolute dimethylformamide is added dropwise at this temperature, with stirring. The mixture is subsequently stirred at 100° C. for 6 hours and is then concentrated by stripping off the diluent under reduced pressure. The residue is taken up in ethyl acetate, the mixture is washed with water and, after drying over sodium sulphate, the solvent is stripped off under reduced pressure. The product which remains is chromatographed over a silica gel column with chloroform as the mobile phase. 28.2 g (39% of theory) of 1-(4-fluorophenyl)-2-(1-chloro-cyclopropyl)-3-(1,2,4-triazol-1-yl)-propan-2-ol are obtained in this manner in the form of a solid substance of melting point 111° C.

Preparation of Precursors:

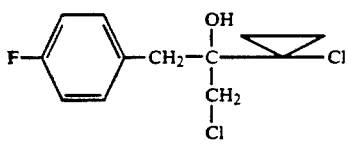

(II-1)

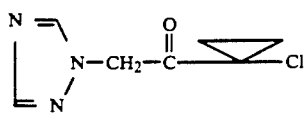

(V-1)

A solution of 65.7 g (0.35 mol) of 4-fluorobenzyl bromide in 430 ml of absolute diethyl ether is added dropwise to a mixture of 9.3 g (0.38 mol) of magnesium filings in 185 ml of diethyl ether at room temperature. The mixture is heated under reflux for 30 minutes, and the solution formed is then added dropwise to a solution of 47.8 g (0.32 mol) of 1-chloro-1-chloroacetyl-cyclopropane in 300 ml of absolute diethyl ether at −78° C., with stirring. The reaction mixture is stirred at −78° C. for 4 hours. Thereafter, it is allowed to warm slowly to 0° C., and a solution of 31 ml of acetic acid in 300 ml of diethyl ether is then added dropwise. The reaction mixture formed is poured onto 1,200 ml of water. The organic phase is separated off, washed with aqueous sodium bisulphite solution and with water, dried over sodium sulphate and concentrated under reduced pressure. 70.6 g (86% of theory) of 1-chloro-2-(1-chlorocyclopropyl)-3-(4-fluoro-phenyl)-propan-2-ol are obtained in the form of an oily product.

$^1$H-NMR (200 MHz, CDCl$_3$): δ=0.6–1.2 (m, 4H); 3.05 (d, 1H); 3.15 (d, 1H); 3.75 (d, 1H); 4.03 (d, 1H); 7.0 (t, 2H); 7.22–7.37 (m, 2H).

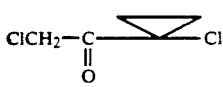

(VIII-1)

40.5 ml (0.5 mol) of sulphuryl chloride are slowly added dropwise to a solution of 54 g (0.46 mol) of 1-acetyl-1-chloro-cyclopropane in 250 ml of methylene chloride at room temperature with stirring. The mixture is stirred first at room temperature for 14 hours and then at 30° C. for 30 minutes. The reaction mixture is then washed with saturated aqueous sodium bicarbonate solution and with water in succession. Thereafter, the organic phase is dried over sodium sulphate and concentrated under reduced pressure. 51.5 g (74% of theory) of 1-chloro-1-chloroacetyl-cyclopropane are obtained in this manner in the form of an oily substance.

$^1$H-NMR (60 MHz, CDCl$_3$): δ=1.2–1.9 (m, 4H); 4.8 (s, 8H).

The compound of the formula

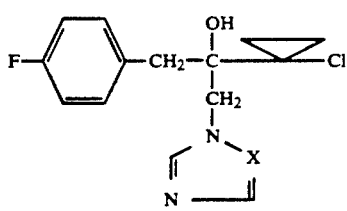

(I-1)

can also be prepared by process (c) according to the invention by reacting (1,2,4-triazol-1-yl-methyl)-(1-chloro-cycloprop-1-yl)-ketone with 4-fluorobenzyl magnesium bromide in the presence of diethyl ether.

Preparation of the starting substance of the formula

A solution of 60 g of 1-acetyl-1-chloro-cyclopropane in 50 ml of acetone is added dropwise to a solution of 50 g of potassium carbonate and 35 g of 1,2,4-triazole in 200 ml of acetone, while stirring at room temperature and under nitrogen atmosphere. The mixture is heated for 8 hours under reflux, then it is concentrated by stripping off the diluent under reduced pressure, the residue is taken up in a mixture of ethyl acetate and toluene, the mixture is washed with water, dried over sodium sulphate and concentrated under reduced pressure, 38.9 g of (1,2,4-triazol-1-yl-methyl)-(1-chloro-cycloprop-1-yl)-ketone are obtained in this manner in the form of a solid substance of melting point 79° C.

$^1$H-NMR (200 MHz, CDCl$_3$): δ=1.50 (m, 2H), 1.78 (m, 2H), 5.62 (s, 2H), 7.98 (s, 1H), 8.14 (s, 1H).

The azolylmethyl-cyclopropyl derivatives of the formula (I) which are shown in the following table are also prepared by the methods which are mentioned in Example 1 and in the description.

TABLE (I)

| Example No. | $Z_m$ | $R^1$ | X | R | Melting point (°C.) |
|---|---|---|---|---|---|
| 2 | 2-F | H | N | Cl | 103 |
| 3 | 2,4-F$_2$ | H | N | Cl | 117 |
| 4 | 2-Cl | H | N | Cl | 108 |
| 5 | 3,4-Cl$_2$ | H | N | Cl | 80–92 |
| 6 | — | H | N | Cl | 81 |
| 7 | 4-Cl | H | N | Cl | 97 |
| 8 | 2,4-Cl$_2$ | H | N | Cl | 159 |
| 9 | 4-CH$_3$ | H | N | Cl | 132 |
| 10 | 3,4-F$_2$ | H | N | Cl | 98 |
| 11 | 4-F | H | CH | Cl | 171 |

The compounds of the formulae shown below were employed as comparison substances in the use examples which follow:

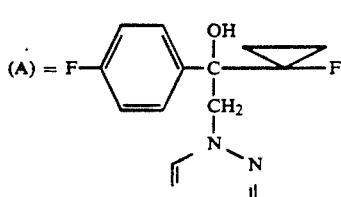

-continued

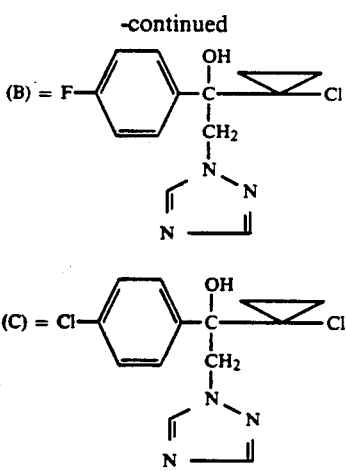

(Known from EP-OS (European Published Specification) 0,180,136).

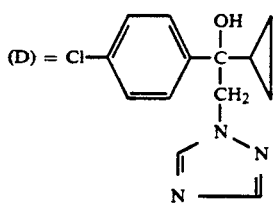

(Known from EP-OS (European Published Specification) 0,015,756).

EXAMPLE A

Botrytis test (bean)/protective
Solvent: 4.7 parts by weight of acetone
Emulsifier: 0.3 parts by weight of alkylaryl polyglycol ether To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound until dripping wet. After the spray coating has dried on, 2 small pieces of agar covered with Botrytis cinerea are placed on each leaf. The inoculated plants are placed in a darkened humid chamber at 20° C. 3 days after the inoculation, the size of the infected spots on the leaves is evaluated.

In this test, the compound (I-1) according to the invention has a considerably better activity than the comparison substances (A) and (C).

EXAMPLE B

Uromyces test (dwarf bean)/protective
Solvent: 4.7 parts by weight of acetone
Emulsifier: 0.3 parts by weight of alkylaryl polyglycol ether.

To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound until dripping wet. After the spray coating has dried on, the plants are inoculated with an aqueous uredospore suspension of the bean rust causative organism (Uromyces appendiculatus) and remain in a dark humidity chamber at 20° to 22° C. and 100% relative atmospheric humidity for 1 day.

The plants are then placed in a greenhouse under intensive illumination at 20° to 22° C. and a relative atmospheric humidity of 70 to 80% for 9 days.

Evaluation is carried out 10 days after the inoculation.

In this test, the compound (I-1) according to the invention has a considerably better activity than the comparison substances (A), (B) and (C).

EXAMPLE C

Venturia test (apple)/protective
Solvent: 4.7 parts by weight of acetone
Emulsifier: 0.3 parts by weight of alkylaryl polyglycol ether To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound until dripping wet. After the spray coating has dried on, the plants are inoculated with an aqueous conidia suspension of the apple scab causative organism (Venturia inaequalis) and then remain in an incubation cabin at 20° C. and 100% relative atmospheric humidity for 1 day.

The plants are then placed in a greenhouse at 20° C. and a relative atmospheric humidity of about 70%.

Evaluation is carried out 12 days after the inoculation.

In this test, the compound (I-1) according to the invention has a considerably better action than the comparison substances (A) and (C).

EXAMPLE D

Pseudocercosporella herpotrichoides test (wheat)/protective
Solvent: 100 parts by weight of dimethylformamide
Emulsifier: 0.25 parts by weight of alkylaryl polyglycol ether To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound until dew moist. After the spray coating has dried on, the plants are inoculated at the stem base with spores of Pseudocercosporella herpotrichoides.

The plants are placed in a greenhouse at a temperature of about 10° C. and a relative atmospheric humidity of about 80%.

Evaluation is carried out 21 days after the inoculation.

In this test, the compound (I-1) according to the invention has a very good activity.

EXAMPLE E

Erysiphe test (barley)/seed treatment

The active compounds are used as dry dressings. These are prepared by extending the particular active compound with a ground mineral to give a finely pulverulent mixture, which ensures uniform distribution on the seed surface.

To apply the dressing, the seed is shaken with the dressing in a closed glass flask for 3 minutes.

3 batches of 12 grains of the barley are sown 2 cm deep in standard soil. 7 days after sowing, when the young plants have unfolded their first leaf, they are dusted with spores of Erysiphe graminis f. sp. hordei.

The plants are placed in a greenhouse at a temperature of about 20° C.